US007588940B2

(12) United States Patent
Grier et al.

(10) Patent No.: US 7,588,940 B2
(45) Date of Patent: Sep. 15, 2009

(54) APPARATUS AND METHOD FOR FABRICATING, SORTING, AND INTEGRATING MATERIALS WITH HOLOGRAPHIC OPTICAL TRAPS

(75) Inventors: David G. Grier, Chicago, IL (US); Eric R. Dufresne, Cambridge, MA (US)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 11/029,396

(22) Filed: Jan. 6, 2005

(65) Prior Publication Data

US 2005/0152039 A1     Jul. 14, 2005

(51) Int. Cl.
    *C12N 15/63*    (2006.01)
(52) U.S. Cl. ............... 435/471; 435/173.5; 435/440
(58) Field of Classification Search ............ 435/173.5, 435/440, 471
    See application file for complete search history.

(56) References Cited

U.S. PATENT DOCUMENTS

| 4,820,015 | A |   | 4/1989  | Mogi          |         |
|-----------|---|---|---------|---------------|---------|
| 5,079,169 | A |   | 1/1992  | Chu et al.    |         |
| 5,674,743 | A | * | 10/1997 | Ulmer         | 435/287.2 |
| 5,682,214 | A |   | 10/1997 | Amako et al.  |         |
| 5,739,879 | A |   | 4/1998  | Tsai          |         |
| 6,055,106 | A |   | 4/2000  | Grier et al.  |         |
| 2002/0115219 | A1 | * | 8/2002 | Kobayashi et al. | 435/470 |

FOREIGN PATENT DOCUMENTS

| WO | WO 99/39223   | 8/1999 |
| WO | WO 99-39223 A | 8/1999 |
| WO | WO 03/008943  | 1/2003 |

OTHER PUBLICATIONS

Nelson, DL et al., ed. Lehninger Principles of Biochemistry, 3rd edition. 2000. Worth Publishers, New York. p. 86.*
Dufresne, ER et al. Computer-generated holographic optical tweezer arrays. Review of Scientific Instruments. Mar. 2001. 72(3): 1810-1816.*
Alex Terray. "Microfluidic Control Using Colloidal Devices." Science, vol. 296, Jun. 7, 2002. pp. 1841-1843.
Pu Chun Ke et al. "Characterlzation of trapping forces in the prsence of spherical aberration" Journal of Modern Optics, vol. 45 No. 10 pp. 2159-2168, 1998.
Felgner et al. "Calibration of light forces in optical tweezers" Applied Optics, vol. 34 No. 6 pp. 977-982 Feb. 20, 1995.
Dufresne et al. "Optical tweezer arrays and optical substrates created with diffrative optics" Review of Scientific Instruments vol. 69 No. 5 pp. 1974-1816.
Galajda et al. "Complex micromachines produced and drive by light" Applied Physics Letters, vol. 78 No. 2 pp. 249-251, Jan. 8, 2001.
Lachish-Zalait et al. "Direct surface patterning from solutions: localized microchemistry using a focused laser" Adv Functional Materials, vol. 11 No. 3 pp. 218-223, Jun. 2001.

Grier "Efficient Implementations of spatially resolved photochemistry using . . . " Dept of Physics, James Franck Inst and Inst of Biophysical Dynamics, U of Chic, Aug. 6, 2001.
Curtis et al. "Precise and automated optical characterization and alignment . . . " Dept of Physics, James Franck Inst and Inst of Biophysical Dynamics, U of Chic Mar. 21, 2002 pp. 1-8.
Grier et al. "Correcting aberrations in dynamic holographic optical traps . . . " Dept of Physics, James Franck Inst and Inst for Biophysical Dynamics, U of Chi, Feb. 15, 2002, pp. 1-4.
Grier et al. "Method for incorporating foreign matter into living cells" Dept of Physics, James Franck Ist and Inst for Biophysical Dynamics, U of Chic Jan. 14, 2002 pp. 1-2.
Grier "Sorting nonabsorbing particles from absorbing particles . . . " Dept of Physics, James Franck Inst and Inst for Biophysical Dynamics, U of Chic Aug. 24, 2001 pp. 1-2.
Korda et al. "Kinetic lick-in in an array of optical tweezers" Dept of Physics, James Franck Inst and Inst for Biophysical Dynamics, U of Chic Jan. 8, 2002 pp. 1-4.
Grier et al. "Patterned anisotropic conductor and sensitive magnetometer" Dept ofPhysics, James Franck Inst and Inst for Biophysical Dynamics, U of Chic Jan. 14, 2002.
Grier "Efficient implementation of spatially resolved photochemistry using . . . " Dept of Physics, James Franck Inst and Inst of Biophysical Dynamics, U of Chic Jan. 21, 2002.
Robert et al. "Finer features for functional microdevices" Nature, vol. 412 pp. 697-698 Aug. 16, 2001.
Dufresne et al. "Computer-generated holographic optical tweezer arrays" Rev of Sci Instruments, vol. 72 No. 3 pp. 1810-1816 Mar. 2001.
Berns, Michael W: "Laser scissors and tweezers" Scientific American, vol. 278, No. 4, Apr. 1998, pp. 62067, XP009028743, ISSN: 0036-8733, the whole document.
Munce et al. "Optical micromanipulation and analysis of single cells on a . . . " Proc of Spie-the Int'l Soc for Opt Eng: Optical Diag of Living Cells V, vol. 4622 pp. 176-182.
Steubing et al. "Laser induced cell fusion in combination with optical tweezers the laser cell fusion trap" Cytometry, vol. 12 No. 6, 1991, pp. 505-510, the whole document.
Dufresne et al. "Optical tweezer arrays and optical substrates created with diffractive optics" Rev of Sci Instr vol. 69 No. 5 May 1998 pp. 1974-1977, abstract.

(Continued)

*Primary Examiner*—Leon B. Lankford, Jr.
*Assistant Examiner*—Susan E. Fernandez
(74) *Attorney, Agent, or Firm*—Jean C. Edwards, Esq.; Akerman Senterfitt (57) ABSTRACT

An apparatus and method for manipulating, effecting interaction of, photochemically transforming and/or sorting small dielectric particles or other materials. The apparatus and method involves use of one or more diffractive optical elements which each receive a laser beam and form a plurality of laser beams. These laser beams are operated on by a telescope lens system and then an objective lens element to create an array of optical traps for manipulating, effecting interaction of, photochemically transforming and/or sorting small dielectric particles or other materials.

8 Claims, 7 Drawing Sheets

OTHER PUBLICATIONS

Grier "A revolution in optical manipulation" Nature vol. 424 No. 6950, Aug. 14, 2003 pp. 810-816 XP002276075 ISSN 0028-0836 the whole document.

Neil et al. "Active aberration correction for the writing of three-dimensional optical memory devices" Applied Optics, vol. 41 No. 7 pp. 1374-1379, Mar. 1, 2002.

Neil et al. "Adaptive aberration correction in a two-photon microscope" Journal of Micorscopy, vol. 200 pt 2, 00. 105-108, Nov. 2000.

Neil et al. "Closed-loop aberration correction by use of a model zernike wave-front sensor" Optics Letters vol. 25 No. 15, pp. 1083-1085 Aug. 1, 2000.

Birch et al. "Real-time optical aberration correction with a ferroelectric liquid-crystal spatial light modulator" Applied Optics vol. 37 No. 11 pp. 2164,2169 Apr. 10, 1998.

Rohrbach et al. "Trapping forces, force constants, and potential depths for dialectric spheres in the presence of . . . " Applied Optics vol. 41 No. 13 pp. 2494-2507 May 1, 2002.

Pu Chun Ke et al. "Characteriziation of trapping forces in the presence of spherical aberration" Journal of Modern Optics, vol. 45 No. 10 pp. 2159-2168, 1998.

Felgner et al. "Calibration of light forces in optical tweezers" Applied Optics, vol. 34 No. 6 pp. 977-982 Feb. 20, 1995.

Dufresne et al. "Optical tweezer arrays and optical subtrates created with diffractive optics" Review of Scientific Instruments vol. 69 No. 5 pp. 1974-1816.

Galajda et al. "Complex micromachines produced and drive by light" Applied Physics Letters, vol. 78 No. 2 pp. 249-251, Jan. 8, 2001.

Lachish-Zalait et al. "Direct surface patterning from solutions: localized microchemistry using a focused laser" Adv Functional Materials, vol. 11 No. 3 pp. 218-223, Jun. 2001.

Robert et al. "Finer features for functional microdevices" Nature, vol. 412 pp. 697-698 Aug. 16, 2001.

Dufresne et al. "Computer-generated holographic optical tweezer arrays" Rev of Sci Instruments, vol. 72 No. 3 pp. 1810-1816 Mar. 2001.

David G. Grier, "A Revolution in Optical Manipulation", Nature, Aug. 14, 2003, vol. 424, p. 810-816, Nature Publishing Group.

Michael W. Berns, "Laser Scissors and Tweezers", Scientific American, Apr. 1998, p. 52-57.

Jennifer E. Curtis, "Dynamic Holographic Optical Tweezers", Optics Communications, Jun. 15, 2002, vol. 207, p. 169-175, Elsevier Science.

* cited by examiner

APPARATUS AND METHOD FOR FABRICATING, SORTING, AND INTEGRATING MATERIALS WITH HOLOGRAPHIC OPTICAL TRAPS

The portion of this invention relating to spatially resolved photochemistry using holographic optical traps was made with U.S. Government support provided by the National Science Foundation through Grant Number DMR-9730189 and by the MRSEC program of the NSF through Grant Number DMR-9880595. The portion of this invention relating to sorting nonabsorbing from absorbing particles using optical traps was made with U.S. Government support provided by the National Science Foundation through Grant Number DMR-9730189.

The present invention is related generally to a method and apparatus for manipulating and modifying small dielectric particles or other materials using the intense illumination and intensity gradients in strongly focused beams of light. In particular, the invention is related to a method and apparatus which uses focused laser light directed by a diffractive optical element, such as a hologram or diffraction grating, to create optical traps or traps and any one of a variety of selectable optical intensity patterns to assemble or direct particulate materials, or other affected materials, into a desired spatial pattern for any one of a myriad of uses. More particularly, the invention is related to methods for manipulating, effecting interaction of, photochemically transforming and/or sorting small dielectric particles or other materials.

It is known to construct an optical trap (i.e., trap) using optical gradient forces from a single beam of light to manipulate the position of a small dielectric particle immersed in a fluid medium whose refractive index is smaller than that of the particle. The optical trap technique has been generalized to enable manipulation of reflecting, absorbing and low dielectric constant particles as well. Likewise, U.S. Pat. No. 6,055,106, co-invented by the inventor named herein and incorporated herein by reference, discloses the manipulation of multiple particles with multiple traps. However, it was previously unknown to use optical traps for the various applications of this invention.

Optical traps, originally described by A. Ashkin et al., have become an established method for trapping, moving and otherwise manipulating mesoscopic volumes of matter. See A. Ashkin et al., "Observation of single-beam gradient force optical trap for dielectric particles,". Optics Letters 11, 288-290 (1986). Central to their operation is minimizing the absorption of trapping light to avoid damaging the trapped material. Optical scalpels operate on the opposite principle, using the energy in a tightly focused laser beam to cut through soft materials. This application discloses and claims a novel hybrid system in which focused beams of laser light operate as optical traps for some nonabsorbing particles in a heterogeneous sample and simultaneously as optical scalpels for others.

Another application of optical trap technology of the invention involves introducing foreign materials into living cells by breaching the cell membrane without causing it to fail entirely, and for moving the materials through the breach. Various methods for accomplishing this have been developed, including viral vectors for transfecting short lengths of DNA, the gene gun and its variants for transferring larger sections, and electroporation for inducing transmembrane diffusion. None appears to be appropriate for transferring physically large materials, particularly if those materials are themselves fragile. The present methods and apparatus described herein solves this and other problems.

In addition, holographic optical traps can be used to effect spatially-resolved photochemistry having several advantages over competing techniques for chemically defining small structures. For example, spatially-resolved photochemistry implemented with optical traps facilitates the creation of three-dimensional structures with features ranging in size from a small fraction of the wavelength of light to macroscopic scales. While techniques such as dip-pen nanolithography and microcontact printing offer superior spatial resolution, they are not amenable to three dimensional fabrication. A very wide variety of photochemical reactions are known, and any of these might be amenable to spatially-resolved photo-fabrication. Thus spatially-resolved photochemistry offers more flexibility than most micro-and nano-fabrication methodologies. Performing spatially-resolved photochemistry with holographic optical traps greatly enhances the utility of the basic approach by greatly improving its efficiency.

It is therefore an object of the invention to provide an improved method and system for simultaneously establishing a plurality of optical traps using a single and/or plurality of devices, such as, for example, multiple holographic optical trap implementations operating simultaneously on a single sample and multiple optical traps and multiple intensity regions operating simultaneously on a single sample.

It is an additional object of the invention to provide a novel method and apparatus for using holograms for generating an optical gradient field for controlling a plurality of particles or other optical media.

It is a further object of the invention to provide an improved method and system for establishing a plurality of optical traps for a variety of commercial applications relating to manipulation of small particles such as in photonic circuit manufacturing, nanocomposite material applications, fabrication of electronic components, opto-electronic devices, chemical and biological sensor arrays, assembly of holographic data storage matrices, facilitation of combinatorial chemistry applications, promotion of colloidal self-assembly, and the manipulation of biological materials.

It is a further object of the invention to provide an improved method and system for using optical traps to incorporate foreign matter into living cells.

It is yet another object of the invention to provided an improved method and system to sort optically nonabsorbing particles from optically absorbing particles.

It is yet another object of the invention to provide an improved method and system to implement the fabrication of heterogeneous structures using spatially resolved photochemistry.

It is still another object of the invention to provide an improved method and system for constructing a temporally and spatially varying configuration of optical gradient fields for various particle sorting applications.

It is also an object of the invention to provide a novel method and system for using one or more laser beams in conjunction with one or more diffractive optical elements for constructing a selectable time varying and/or particular spatial array of optical traps for manipulating a dielectric metallic materials and other materials.

It is yet a further object of the invention to provide an improved method and system using a single input laser beam, a diffractive optical element, and a converging lens to form a static or dynamic optical trap which, in conjunction with other so formed optical traps can be used to manipulate, effect interaction of, photochemically transform and/or sort small dielectric particles or other materials.

It is also a further object of the invention to provide an improved method and system employing a laser beam input to a diffractive optical element with a beam scanning system enabling scanning of an array of optical traps for various commercial applications.

It is in addition another object of the invention to provide a novel method and apparatus for constructing an optical trap configuration using a laser beam, a diffractive optical element and a converging optical system to form the trap configuration at a selectable location relative to an objective lens focal plane.

It is yet another object of the invention to provide a novel method and apparatus for using a laser beam input to a diffractive optical element to generate a three-dimensional arrangement of optical traps.

It is another object of the invention to provide a novel method for creating multiple independently steered optical traps using a time-dependent addressable phase-shifting medium (such as a liquid crystal phase shifting array or other phase medium) as a diffractive optical element.

It is a further object of the invention to provide a novel method for creating time-dependent optical gradient fields for the segregation of microscopic particles.

It is yet another object of the invention to provide a novel method for manipulating a plurality of biological objects including the crystallization of proteins or implementing other phase changes.

Other objects, features and advantages of the present invention will be readily apparent from the following description of the preferred embodiments thereof, taken in conjunction with the accompanying drawings described below wherein like elements have like numerals throughout.

DETAILED DESCRIPTION OF THE INVENTION

Figure 1:
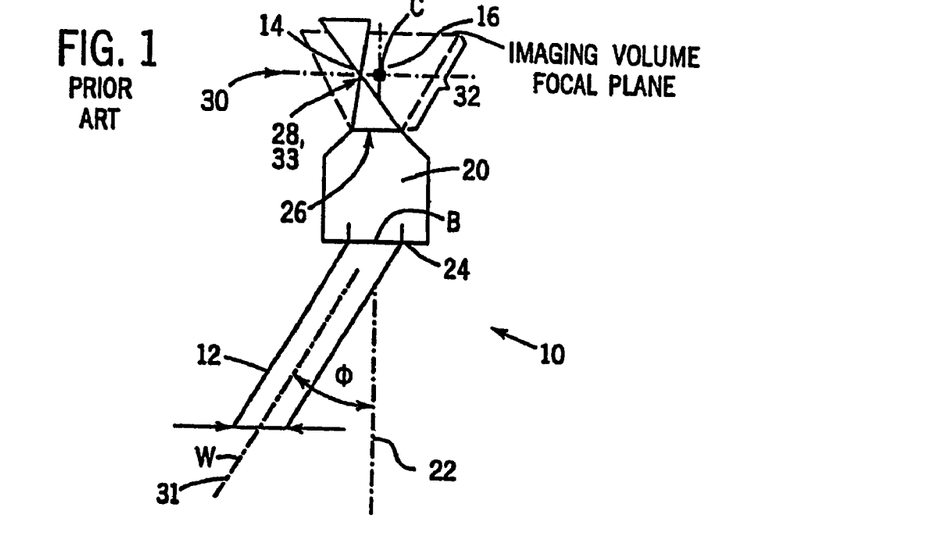
FIG. 1 illustrates a prior art method and system for a single optical trap.
Figure 2:
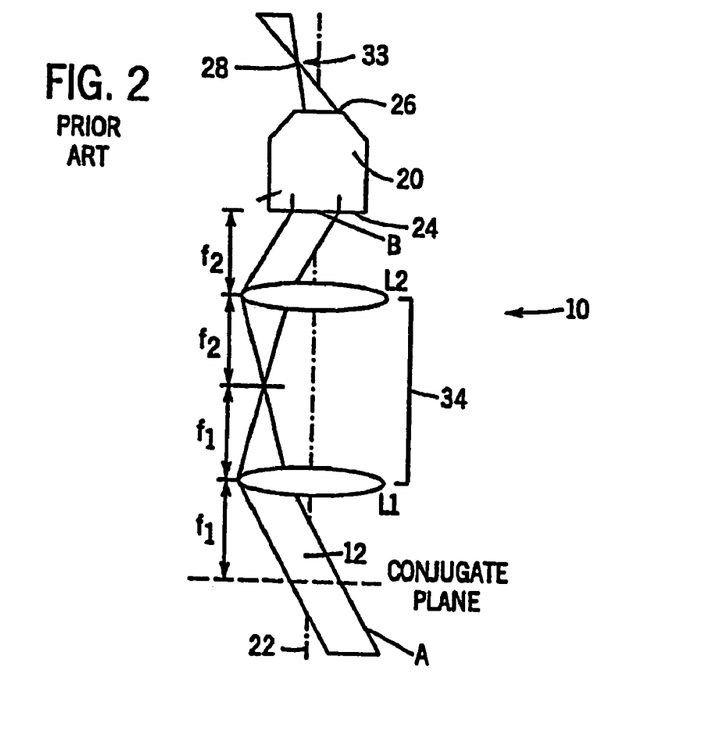
FIG. 2 illustrates a prior art method and system for a single, steerable optical trap.

This invention presents several uses for the "Apparatus for Applying Optical Gradient Forces" disclosed and claimed in U.S. Pat. No. 6,055,106 to Grier et al. That apparatus is encompassed by use of the terminology optical trap, and optical gradient force trap hereinafter. By way of introduction, FIGS. 1 and 2 illustrate several prior art methods and systems. These systems will first be reviewed; and then the methods of the present invention will be described in terms of the optical trap embodiment examples of FIGS. 3-7A and 7B. In the prior art optical trap system 10 of FIG. 1, optical gradient forces arise from use of a single beam of light 12 to controllably manipulate a small dielectric particle 14 dispersed in a medium 16 whose index of refraction is smaller than that of the particle 14. The nature of the optical gradient forces is well known, and also it is well understood that the principle has been generalized to allow manipulation of reflecting, absorbing and low dielectric constant particles as well.

The optical trap system 10 is applied by using a light beam 12 (such as a laser beam) capable of applying the necessary forces needed to carry out the optical trapping effect needed to manipulate a particle. The method used to create a conventional form of the optical trap 10 is to project one or more beams of light, each with a specified degree of collimation, through the center of a back aperture 24 of a converging optical element (such as an objective lens 20). As noted in FIG. 1 the light beam 12 has a width "w" and having an input angle, $\Phi$, relative to an optical axis 22. The light beam 12 is input to a back aperture 24 of the objective lens 20 and output from a front aperture 26 substantially converging to a focal point 28 in focal plane 30 of imaging volume 32 with the focal point 28 coinciding with an optical trap 33. In general, any beam of light brought to a diffraction-limited focus, and possessing sufficiently large axial intensity gradients to trap a particle stably against axial radiation pressure, can form the basis for the optical trap system 10.

Creating such a focus requires a focusing element with sufficiently high numerical aperture and sufficiently well-corrected aberrations. Generally, the minimum numerical aperture to form a trap is about 0.9 to about 1.0.

In the case of the light beam 12 being a collimated laser beam and having its axis coincident with the optical axis 22, the light beam 12 enters the back aperture 24 of the objective lens 20 and is brought to a focus in the imaging volume 32 at the center point c of the objective lens focal plane 30. When the axis of the light beam 12 is displaced by the angle $\Phi$ with respect to the optical axis 22, beam axis 31 and the optical axis 22 coincide at the center point B of the back aperture 12. This displacement enables translation of the optical trap across the field of view by an amount that depends on the angular magnification of the objective lens 20. The two variables, angular displacement $\Phi$ and varying convergence of the light beam 12, can be used to form the optical trap at selected positions within the imaging volume 32. A multiple number of the optical traps 33 can be arranged in different locations provided that multiple beams of light 12 are applied to the back aperture 24 at the different angles $\Phi$ and with differing degrees of collimation.

In order to carry out optical trapping in three dimensions, optical gradient forces exerted on the particle to be trapped must exceed other radiation pressures arising from light scattering and absorption. In general this necessitates the wave front of the light beam 12 to have an appropriate shape at the back aperture 24. For example, for a Gaussian $TEM_{00}$ input laser beam, the beam diameter, w, should substantially coincide with the diameter of the entrance pupil 24. For more general beam profiles (such as Laguerre-Gaussian modes) comparable conditions can be formulated.

In another prior art system in FIG. 2, the optical trap system 10 can translate the optical trap 33 across the field of view of the objective lens 20. A telescope 34 is constructed of lenses L1 and L2 which establishes a point A which is optically conjugate to the center point B in the prior art system of FIG. 1. In the system of FIG. 2 the light beam 12 passing through the point A also passes through the point B and thus meets the basic requirements for performing as the optical trap system 10. The degree of collimation is preserved by positioning the lenses L1 and L2 as shown in FIG. 2, their focal lengths and other optical characteristics being selected to optimize the transfer properties of the telescope 34. In particular, the magnification of the telescope 34 can be chosen to optimize angular displacement of the light beam 12 and its width w in the plane of the back aperture 24 of the objective lens 20. As stated hereinbefore, in general several of the light beams 12 can be used to form several associated optical traps. Such multiple beams 12 can be created from multiple independent input beams or from a single beam manipulated by conventional reflective and/or refractive optical elements.

Figure 3:
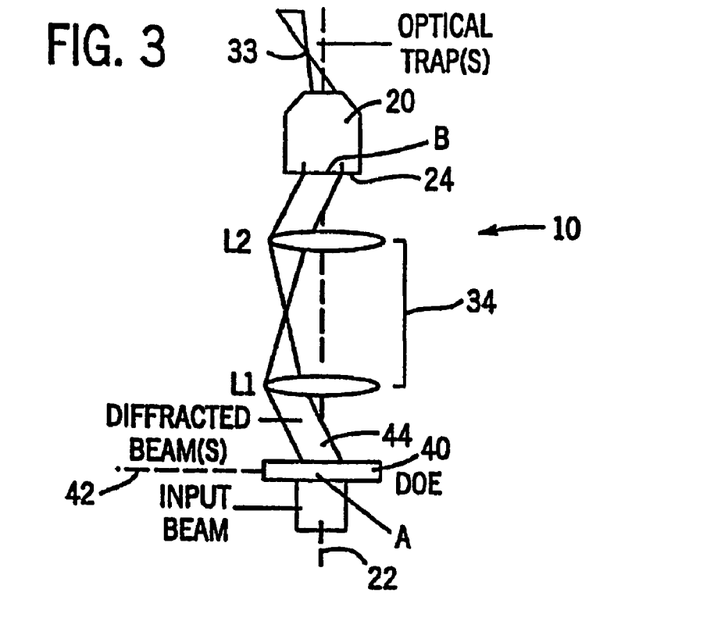
FIG. 3 illustrates a method and system using a diffractive optical element.

In one optical trap configuration, shown in FIG. 3, arbitrary arrays of optical traps can be formed. A diffractive optical element 40 is disposed substantially in a plane 42 conjugate to back aperture 24 of the objective lens 20. Note that only a single diffracted output beam 44 is shown for clarity, but it should be understood that a plurality of such beams 44 can be created by the diffractive optical element 40. The input light beam 12 incident on the diffractive optical element 40 is split into a pattern of the output beam 44 characteristic of the nature of the diffractive optical element 40, each of which emanates from the point A. Thus the output beams 44 also pass through the point B as a consequence of the downstream optical elements described hereinbefore. In some situations, where it is desired to create a plurality of objects in a specific spatial relationship to one another, with each object in a specific orientation, it will be necessary to create the plurality of objects on a timescale faster than that on which relevant motion of the objects occurs. This timescale will be a function of, among other factors the viscosity of the medium. In such a situation, an apparatus which allows fabrication of the plurality of objects in parallel may provide an advantage over one which fabricates the objects sequentially.

The diffractive optical element 40 of FIG. 3 is shown as being normal to the input light beam 12, but many other arrangements are possible. For example, in FIG. 4 the light beam 12 arrives at an oblique angle β relative to the optic axis 22 and not at a normal to the diffractive optical element 40. In this embodiment, the diffracted beams 44 emanating from point A will form optical traps 50 in focal plane 52 of the imaging volume 32 (seen best in FIG. 1). In this arrangement of the optical trap system 10 an undiffracted portion 54 of the input fight beam 12 can be removed from the optical trap system 10. This configuration thus enables processing less background light and improves efficiency and effectiveness of forming optical traps.

The diffractive optical element 40 can include computer generated holograms which split the input light beam 12 into a preselected desired pattern. Combining such holograms with the remainder of the optical elements in FIGS. 3 and 4 enables creation of arbitrary arrays in which the diffractive optical element 40 is used to shape the wavefront of each diffracted beam independently. Therefore, the optical traps 50 can be disposed not only in the focal plane 52 of the objective lens 20, but also out of the focal plane 52 to form a three-dimensional arrangement of the optical traps 50.

Figure 4:
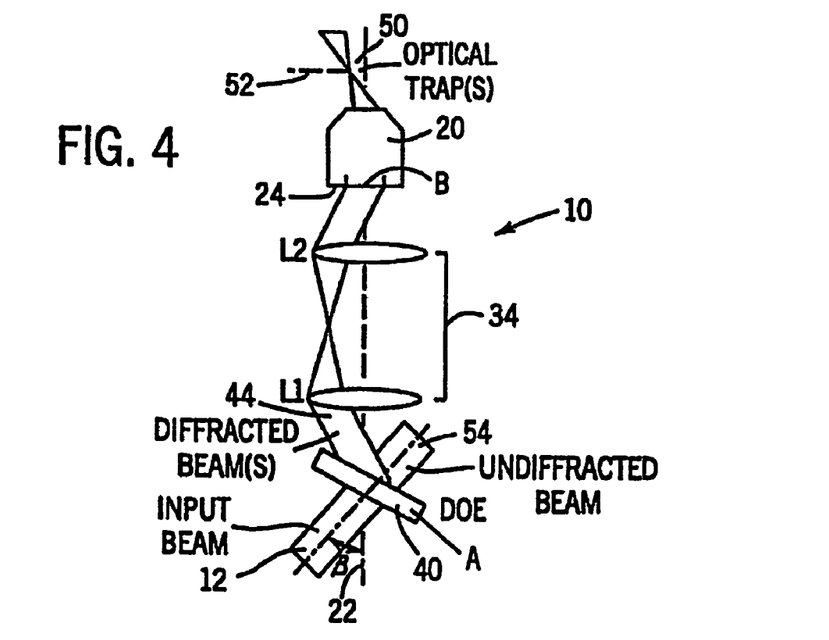
FIG. 4 illustrates another method and system using a tilted optical element relative to an input light beam.

In the optical trap system 10 of FIGS. 3 and 4, also included is a focusing optical element, such as the objective lens 20 (or other like functionally equivalent optical device, such as a Fresnel lens) to converge the diffracted beam 44 to form the optical traps 50. Further, the telescope 34, or other equivalent transfer optics, creates a point A conjugate to the center point B of the previous back aperture 24. The diffractive optical element 40 is placed in a plane containing point A.

In another embodiment, arbitrary arrays of the optical traps 50 can be created without use of the telescope 34. In such an embodiment the diffractive optical element 40 can be placed directly in the plane containing point B. In another form of the invention, one of the lenses can be positioned in the hologram itself rather than in the telescope 34.

In the optical trap system 10 either static or time dependent diffractive optical elements 40 can be used. For a dynamic, or time dependent version, one can create time changing arrays of the optical traps 50 which can be part of a system utilizing such a feature. In addition, these dynamic optical elements 40 can be used to actively move particles and other materials with diverse optical properties relative to one another. For example, the diffractive optical element 40 can be a liquid crystal spatial light modulator encoding computer-generated phase modulations onto the wavefront of an incident laser beam. In another embodiment, a spatial light modulator may also be used in conjunction with a phase ring in place of the diffractive optical element.

Figure 5:
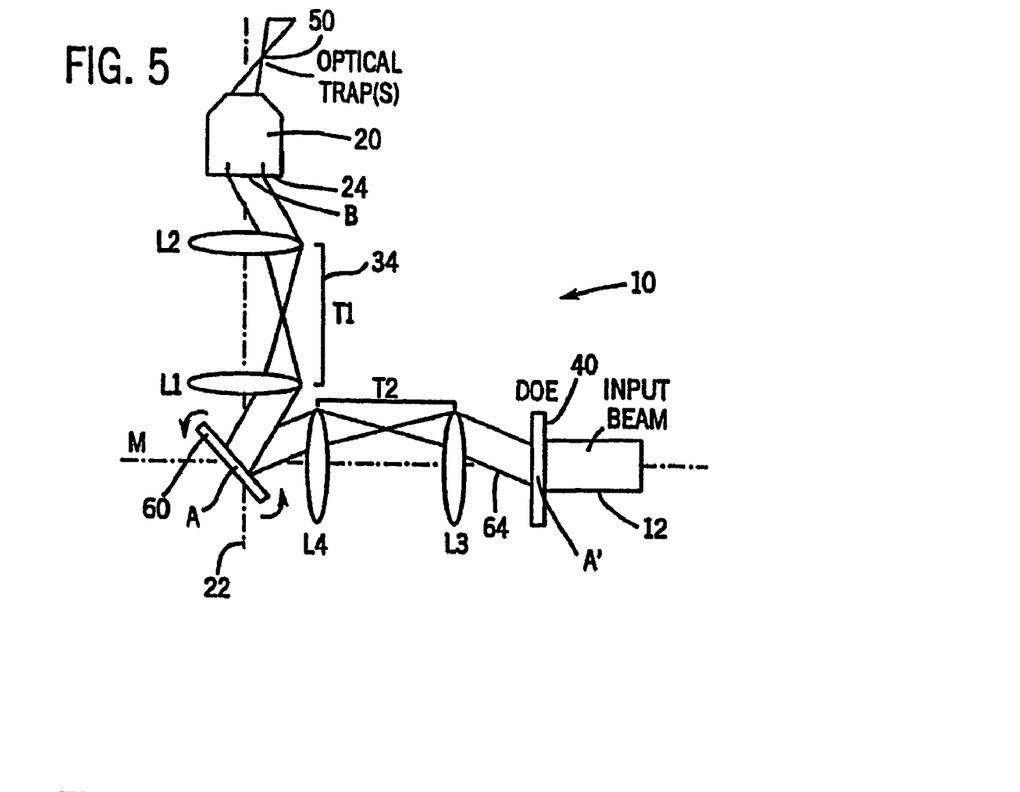
FIG. 5 illustrates a continuously translatable optical trap array using a diffractive optical element.

In another embodiment illustrated in FIG. 5, a system can be constructed to carry out continuous translation of the optical trap 50. A gimbal mounted mirror 60 is placed with its center of rotation at point A. The light beam 12 is incident on the surface of the mirror 60 and has its axis passing through point A and will be projected to the back aperture 24. Tilting of the mirror 60 causes a change of the angle of incidence of the fight beam 12 relative to the mirror 60, and this feature can be used to translate the resulting optical trap 50. A second telescope 62 is formed from lenses L3 and L4 which creates a point A' which is conjugate to point A. The diffractive optical element 40 placed at point A' now creates a pattern of diffracted beams 64, each of which passes through point A to form one of the trap 50 in an array of the optical traps system 10.

In operation of the embodiment of FIG. 5, the mirror 60 translates the entire trap array as a unit. This methodology is useful for precisely aligning the optical trap array with a stationary substrate, for dynamically stiffening the optical trap 50 through small-amplitude rapid oscillatory displacements, as well as for any application requiring a general translation capability.

The array of the optical traps 50 also can be translated vertically relative to the sample stage (not shown) by moving the sample stage or by adjusting the telescope 34. In addition, the optical trap array can also be translated laterally relative to the sample by moving the sample stage. This feature would be particularly useful for movement beyond the range of the objective lens' field of view.

Figure 6:
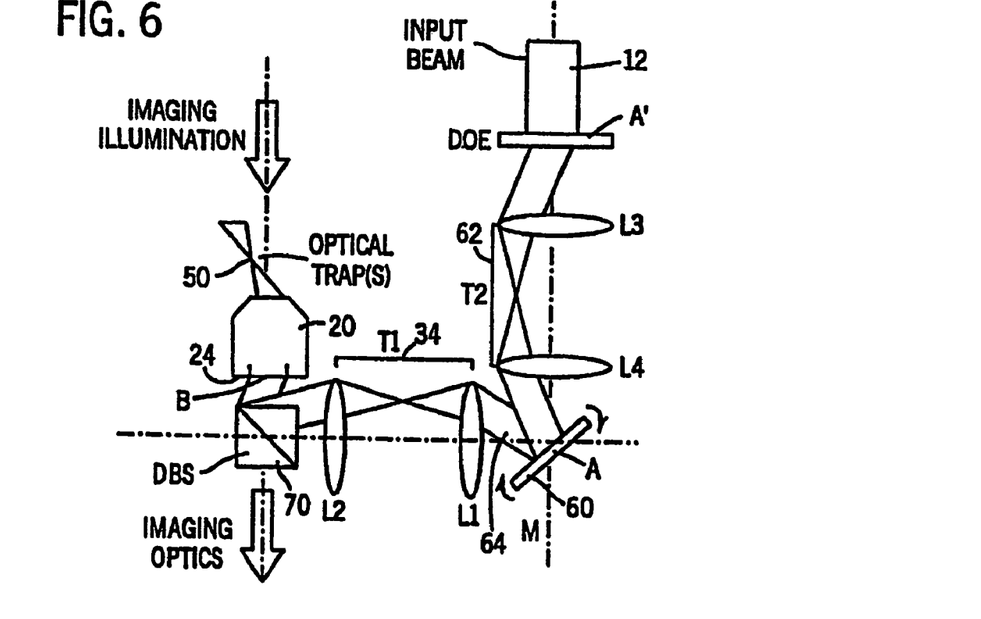
FIG. 6 illustrates a method and system for manipulating particles using an optical trap array while also forming an image for viewing the optical trap array.
Figure 7A:
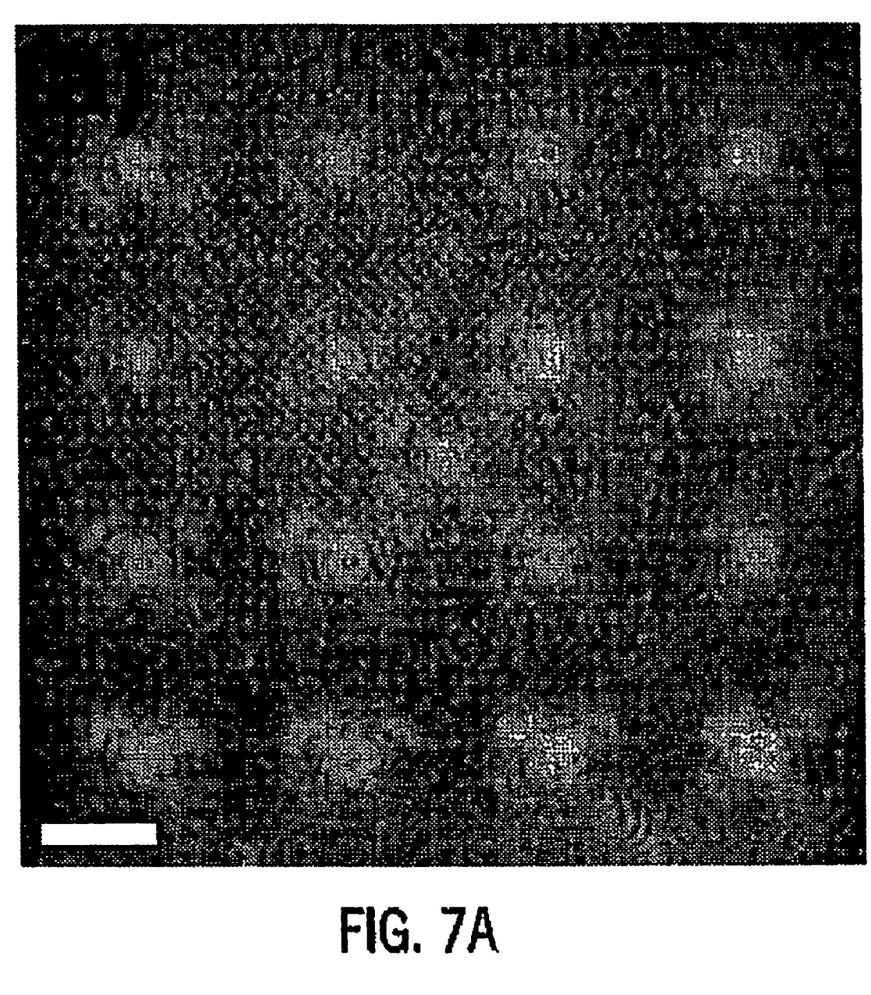
FIG. 7A illustrates an image of a four by four array of optical traps using the optical system of FIG. 6.
Figure 7B:
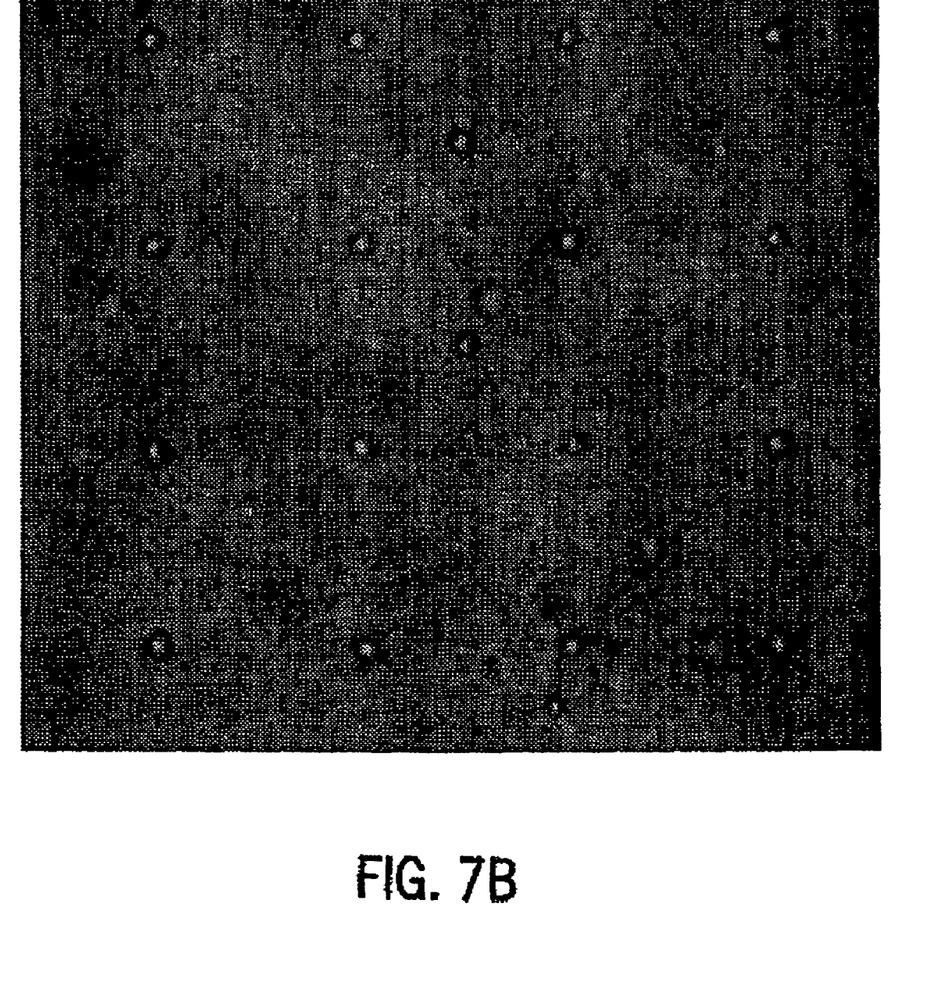
FIG. 7B illustrates an image of one micrometer diameter silica spheres suspended in water by the optical traps of FIG. 7A immediately after the trapping illumination has been extinguished, but before the spheres have diffused away.

In another embodiment shown in FIG. 6, the optical system is arranged to permit viewing images of particles trapped by the optical traps 10. A dichroic beamsplitter 70, or other equivalent optical beamsplitter, is inserted between the objective lens 20 and the optical train of the optical trap system 10. In the illustrated embodiment, the beamsplitter 70 selectively reflects the wavelength of light used to form the optical traps 50 which is reflected to the back aperture 24 with high efficiency while light beam 66 used to form images can pass through to imaging optics.

In yet another embodiment of the invention a method for incorporating foreign matter into living cells is described. It has been determined recently that optical trap devices can be advantageously used to incorporate foreign matter such as an artificial chromosome, into living cells using a combination of optical trapping, optically induced membrane fusion and optical cutting. By way of nonlimiting example, the method includes the steps of encapsulating the material to be transferred in, for example, a liposome, fusing the liposome to the cell membrane, and puncturing the juncture to effect transfer. The first step takes advantage of any of a variety of known possible encapsulation techniques. Once encapsulation is complete, the liposome can be captured with optical traps and translated toward a target cell. Depending on the material's sensitivity to light, several separate optical traps might be preferable to one, in which case holographic optical traps offer advantages to other techniques, such as scanned optical traps.

Unlike scanned optical traps which address multiple trapping points in sequence, and thus are time-shared, holographic optical traps illuminate each of their traps continuously. For a scanned optical trap to achieve the same trapping force as a continuously illuminated trap, it must provide at least the same time-averaged intensity. This means that the scanned trap has to have a higher peak intensity by a factor proportional to at least the number of trapping regions. This higher peak intensity increases the opportunities for optically-induced damage in the trapped material. This damage can arise from at least three mechanisms: (1) single-photon absorption leading to local heating, (2) single-photon absorption leading to photochemical transformations, and (3) multiple-photon absorption leading to photochemical transformations. Events (1) and (2) can be mitigated by choosing a wavelength of light which is weakly absorbed by the trapping material and by the surrounding fluid medium. Event (3) is a more general problem and is mitigated in part by working with longer-wavelength light. Multiple-photon absorption, the central mechanism of the photopolymerization part of this disclosure, occurs at a rate proportional to the intensity raised to a power (i.e., $I^2$ for two-photon absorption). The rates for such processes are rapidly reduced to acceptable levels by reducing the peak intensity of the trapping beam. As a result, lower intensity, continuously-illuminated holographic optical traps are preferable to time-shared scanned traps. Furthermore, the holographic optical trap method lends itself to distributing more independent traps throughout the volume of an extended object than does any scanned trap technique. In particular, holographic optical traps can distribute traps across an object's three-dimensional contours, unlike scanned traps which are limited to a single plane.

Distributing the trapping force among multiple sites on an object further permits holographic optical traps to minimize the maximum intensity and maximum force applied to any one point of the object. This may be thought of as being analogous to a bed of nails, in which any one nail could cause damage, but distributing the loading among multiple nails reduces the local force below the threshold for damage.

Consequently, holographic optical traps offer substantial benefits over both scanned traps and individual conventional optical traps. If the cell itself is motile, it also may be held in place and oriented with holographic optical traps. For some applications, for example when material must be transferred to a particular part of a cell while bypassing others, optical trap manipulation offers advantages. A single set of holographic optical traps can be used to hold both the cell and the liposome simultaneously.

Figure 8A:
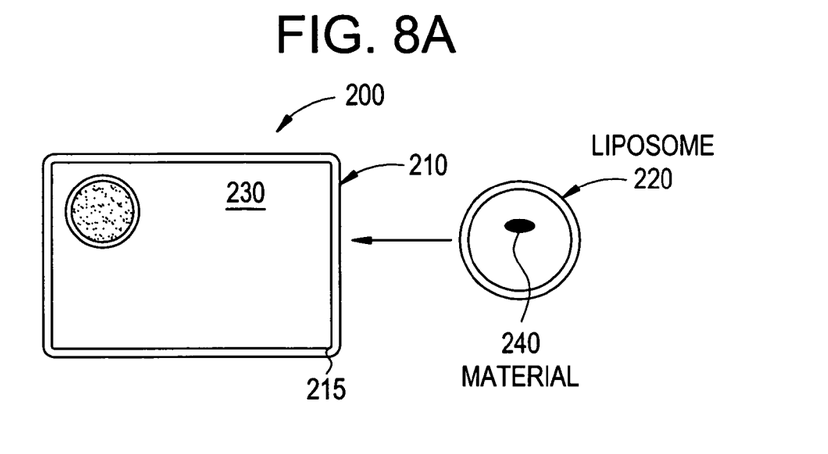
FIG. 8A illustrates a first step in transferring material into a cell with material encapsulated in a liposome being immobilized with optical traps.
Figure 8B:
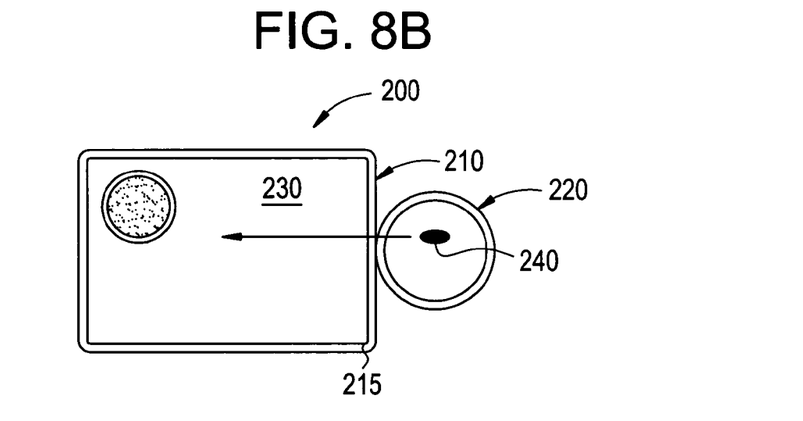
FIG. 8B illustrates a liposome being fused to a cell membrane.
Figure 8C:
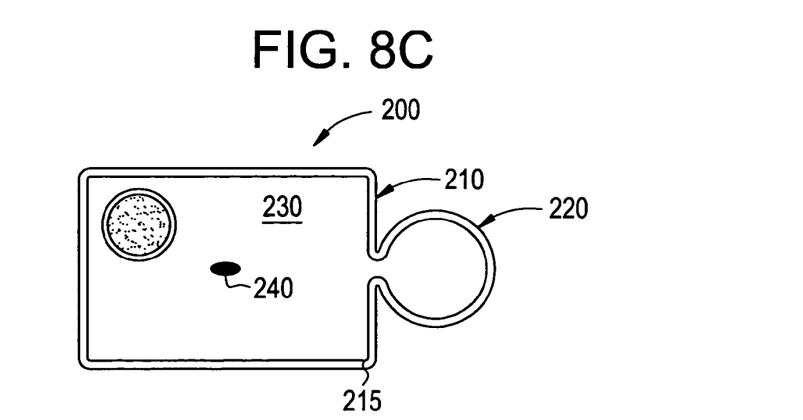
FIG. 8C the material in the liposome is transferred through a breach in the liposome cell function.

As shown in FIG. 8C a cell 200 has an impermeable wall 210, as for example in a plant cell. An optical scalpel can be used to cut away enough of the wall 210 to expose a region of cell membrane 215 for subsequent liposome fusion. The laser used for this cutting or ablation most likely will operate at a shorter wavelength than that used for holding and moving a liposome 220 and the cell 200. Unlike trapping, where material damage is usually undesirable, cutting requires strong interaction between the focused light and the material. Consequently, the conditions discussed above for minimizing damage also provide a guide to optimizing desired damage. In particular, shorter wavelength light carries more energy per photon than longer wavelength light. Each photon absorption therefore is more likely to deliver enough energy to disrupt chemical bonds and to rearrange macromolecules in the cell wall 210 and the cell membrane 215. The rate of all such transformations is increased in shorter wavelength light.

Once an appropriate section of the cell membrane 215 has been exposed, the liposome 220 can be moved into proximity, again using optical trap forces (see FIG. 8A). Fusion can be accomplished either chemically, through the action of proteins or other biochemical agents incorporated into the liposome's outer leaf, or optically through one or more pulses of light directed at the liposome-membrane interface (see FIG. 8B).

Fusion can proceed to effect the transfer in one step, or else further chemical treatment or additional pulse of light may be required to breach the membrane-liposome interface. Once the interface is breached, the liposome's contents (material 240) can transfer into the cell 200 through diffusion, or else can be moved into the cell 200 with one or more of the optical traps. In addition, for artificial chromosomes, for example, the material 240 can be placed directly into cell nucleus 220 by using the optical traps to transfer the matter through the cell membrane 215 and cytoplasm and, thereafter, cutting the nuclear membrane to effect transfer into the nucleus 220 directly.

Once transfer is complete, the cell 200 can be held in place for further observation before being collected. Both holding and collection can be facilitated by optical trap manipulation, particularly if the entire process described above takes place in a closed microfluidic system.

The entire process, from sample selection to cell collection can be carried out using a conventional light microscope for observation. Indeed, the same optical train used to create the optical traps and scalpel for this process also can be used to monitor its progress. It furthermore, all steps are carried out using holographic optical traps, or a related manipulation technique, then the entire process also can be automated, with digitally recorded microscope images being used to program the pattern of optical traps and their motions.

The substance or the material 240 to be introduced into the cell 200 can be any substance and will preferably not be endogenous to the cell 200 into which it is to be introduced. Preferably the substance is a substance not normally able to cross the cell membrane. It is preferred that the substance to be introduced into the cell 200 is a hydrophilic substance, however the substance may also be hydrophobic. Any biological molecule or any macromolecule, for example, a complex of molecules, can be introduced into the cell 200. The material 240 generally has a molecular weight of 100 daltons or more. In a more preferred embodiment, the material 240 is a nucleic acid molecule such as DNA, RNA, PNA (e.g. cDNA, genomic DNA, a plasmid, a chromosome, an oligonucleotide, a nucleotide sequence, or a ribozyme) or a chimeric molecule or a fragment thereof, or an expression vector. Additionally, the material 240 may be any bio-active molecule such as a protein, a polypeptide, a peptide, an amino acid, a hormone, a polysaccharide, a dye, or a pharmaceutical agent such as drug.

Although this discussion has focused on methods for modifying a single cell using the contents of a single liposome, the same approach could be used to fuse multiple liposomes to a single cell, and to process multiple cells simultaneously.

Figure 9:
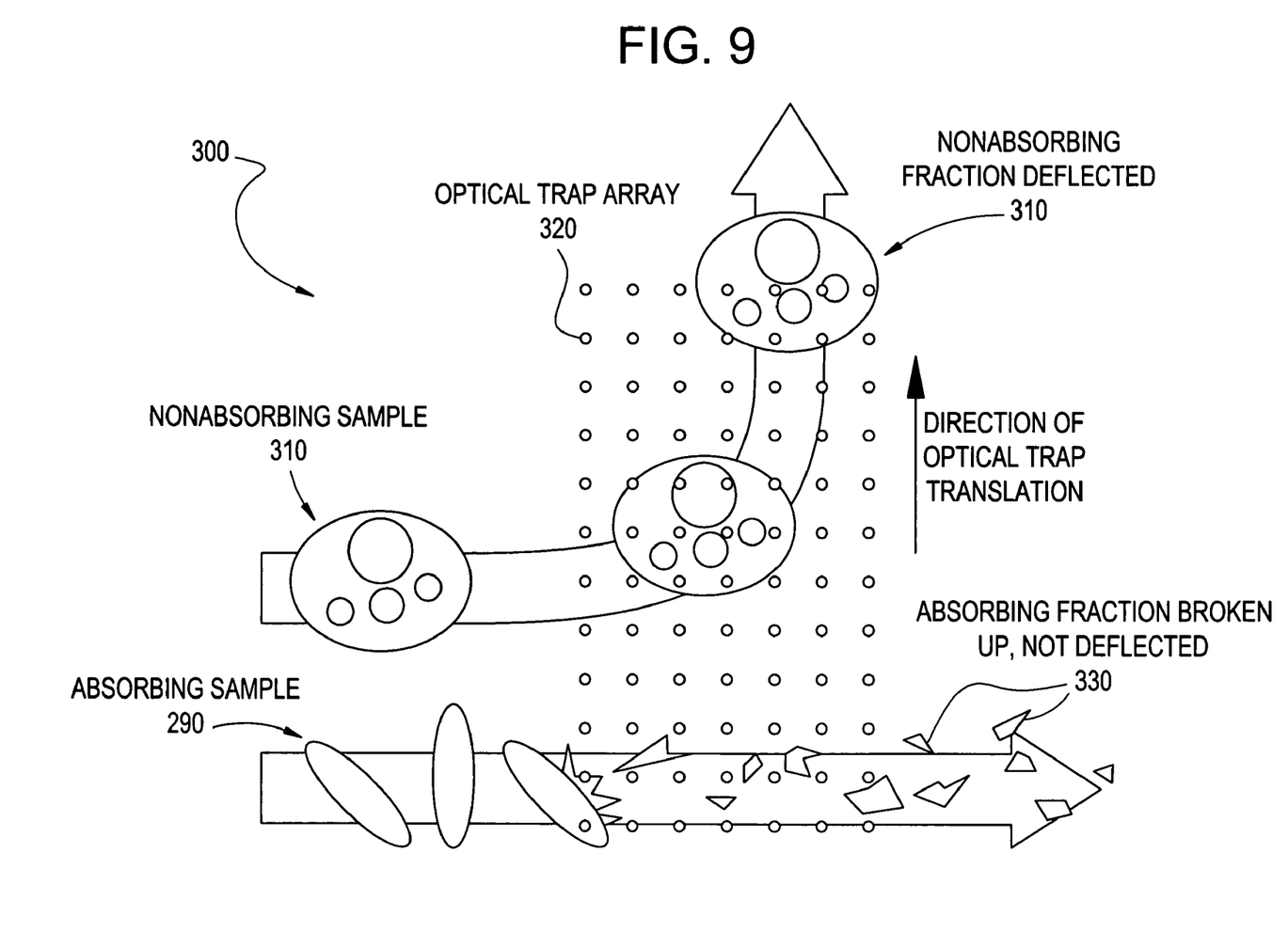
FIG. 9 is a functional block flow diagram illustrating separation of nonabsorbing from absorbing particles.

In another form of the invention a system and method are provided for sorting nonabsorbing particles from absorbing particles 290 is constructed (see FIG. 9). It has been discovered that an optical trap or trap array 300 can be advantageously formed from focused beams of laser light which operate as optical traps for some nonabsorbing particles 310 in a sample and as optical scalpels for others. Rather than precisely cutting the absorbing particles 290 as traditionally done by an optical scalpel, however, absorption of light is used to obliterate the absorbing particles 290 nonspecifically so as to reduce them to very small pieces 330. These small pieces then can be separated from the undamaged nonabsorbing particles left behind in optical traps 320.

An example of the utility of this method is the problem of searching for cancerous cells in a sample of blood. Ordinarily, the vast number of red blood cells in the sample would have to be separated from the candidate cancer cells before testing can begin. Light from optical traps operating in the visible range of wavelengths, for example at a wavelength of 532 nm, would be absorbed strongly by red blood cells and consequently can be used to destroy them through local heating. Other unpigmented cells, however, can be trapped by the same visible traps and manipulated for further testing. Consider, for example, an array of visible optical traps arranged with their characteristic spacing considerably smaller than the size of aired blood cell. A mixture of cells driven through this array of optical traps by an externally mediated fluid flow would encounter these optical traps. The strongly-absorbing cells would be reduced to much smaller components, such as membrane fragments through their interaction with the light. These smaller components would have a comparatively weaker interaction with the light and a small portion might be trapped by some of the traps in the array. More likely, however, they would be washed away by the fluid flow. Rather than being damaged by the light, weakly absorbing cells would encounter one or more optical traps in the array and experience a trapping force.

The intact cells would have larger and more numerous regions susceptible to optical trapping than the fragments of the destroyed cells, and therefore would be preferentially trapped by the array of optical traps. Cells localized in the array of optical traps can be transported for collection by moving the optical traps themselves, for example taking advantage of the features of an earlier application of the assignee herein, (Grier et al., application Ser. No. 09/875,812 which is incorporated by reference herein.) by moving the sample container to transport the trapped cells to a collection region within the sample container, or by periodically turning off the traps and directing the cells through a flow of fluid to a collection area. In any of these ways, the cells which do not absorb light are collected separately from the cells that do.

This approach can be generalized from sorting cells to sorting any other material whose absorption coefficients differ substantially for at least one particular wavelength of light. The benefits of this manipulation include excellent fidelity for rejecting the undesired absorbing material, and the ability to perform other active sorting steps. The same benefits would accrue to other applications of this ablative particle sorting method.

In preferred embodiments of optically ablative particle sorting, separation of nonabsorbing particles can be effected with multiple optical traps created with the holographic optical trap technique. Separation of the trapped particles from the obliterated absorbing particles could be performed with the previously disclosed techniques of active trap manipulation, optical peristalsis, or passive lateral deflection in a flow. The separation could also be performed in a microfluidics device with one channel for flushing waste products from the obliteration of absorbing particles and other channels for collecting selected nonabsorbing particles.

In previous uses of optical traps, great care was required to select a wavelength of light which would not damage any of the material to be trapped. In the present invention, the goal is to select a wavelength which is absorbed strongly by the unwanted subpopulation of a mixed sample, and very weakly by the other subpopulation to be retrieved. Retrieval of the weakly absorbing subpopulation proceeds through conventional methods, and the separation in this case being effected through the passive destruction of the unwanted fraction, rather than through active selection. This could also be a preprocessing step for other analytical methods such as flow cytometry.

By way of nonlimiting example, this method could be used for early detection of cancer through blood screening. To wit, several kinds of cancers in their earliest stages do not form particularly well defined tumors but, instead, define regions of abnormal cells which tend to slough into the bloodstream. In practice, detection of those cells would provide an indication that the patient has an early stage cancer. Such detection would provide at least a tentative diagnosis long before other methods requiring detection of a complete tumor or its metabolic products. Thus, this method would provide for early and more effective treatment. This can be compared with conventional separation methods of centrifugation to separate the denser, hemoglobin-bearing red blood cells from other cells carried in the blood. However, centrifugation often entrains the lighter cells with the heavier ones, thus making detection very difficult.

Using the method of the present invention, blood samples can be made to flow through an array of optical traps having wavelength and intensity that will destroy the cellular structure of the red blood cells, leaving non-red cells, such as white blood cells and possible cancer cells, intact. In fact, the red blood cells will be reduced to fragments too small to trap. In contrast, the undamaged cells can be trapped by the optical traps and transported, for example, by sequentially updating the pattern of traps, to a collection point for subsequent analysis.

In yet another embodiment of the invention a method concerns implementing spatially resolved photochemistry. Light can provide the activation energy for photochemical reactions, and in cases where one photon does not carry enough energy to initiate a photochemical reaction. The photochemical reaction still can proceed if two or more photons are absorbed simultaneously, such that the combined energy of all absorbed photons exceeds the activation threshold for the reaction. The rate at which multi-photon processes proceed depends nonlinearly on the intensity of the available light, with two-photon absorption occurring at a rate proportional to $I^2$, the square of the light's intensity. This nonlinear dependence on intensity can be used to initiate photochemical reactions only in selected volumes within a larger sample and to proceed in a spatially resolved manner. The reaction only takes place in regions which are illuminated sufficiently intensely, and not in others.

Optical traps are tightly focused beams of light and, therefore, offer an ideal method for producing spatially resolved structures through photochemistry. The focal point in an optical trap is the most intense region of the illumination field. Tuning the intensity of this focal region close to the threshold for an appreciable rate of photochemical transformation facilitates controlled photochemistry in a volume comparable to the diffraction-limited focal volume of the optical trap. Whereas optical traps generally are used to trap and manipulate small volumes of matter, here they are being used to transform matter in desirable ways. Single optical traps have been used in the art to create locally intense illumination for initiating and propagating two-photon photochemistry to create photopolymerized devices as small as 10 micrometers in diameter. Defining photochemical patterns in previous conventional methods required either translating a single optical trap through the fluid precursor, or translating the fluid past the single stationary trap. In either case, the process of creating a structure by spatially-resolved photochemistry involved sequentially illuminating target volumes.

Unlike prior methods the present invention uses multiple holographic optical traps to perform spatially resolved photochemistry at multiple locations simultaneously to create structures composed of either heterogeneous or homogeneous materials. For example, in previous methods, one can use the multiple beams to draw multiple copies of the same structure at once, thus allowing the fabrication of multiple identical structures simultaneously. Alternatively, one could use multiple beams of light to simultaneously create different aspects of a single structure, thus allowing it to be made much more rapidly. Finally, separate beams can be used to create the outside structure around an extended volume and to simultaneously created interior volume structures (i.e., structures inside the separately created shell around the volume). Common to all of those techniques is the creation of a structure constituted from a homogeneous material such as a gel. Here, unlike the prior art, the unique combination of the manipulation of the optical traps and the chemical transformations effected thereby, also permit the creation of single or multiple heterogeneous structures. For example, where certain objects are preformed, particular optical traps can be used to hold them in place while other similarly focused beams of light are used to create interconnections made of photochemically transformed materials, thereby creating heterogeneous structures.

Moreover, unlike conventional optical traps, holographic optical traps use computer-generated diffractive optical elements to define multiple optical traps in any user-specified pattern in three dimensions. Each focal point in such a trapping pattern can be used to induce photochemical transformations. Computer algorithms permit placement of one or more optical traps anywhere within a three-dimensional accessible volume, and also permit independent modification of the properties of each of those traps. Creating a new configuration with the traps at a location displaced from the old trap, or where the trap properties are slightly different, can be effected by calculating and projecting a new hologram. A fixed arrangement of traps therefore can be steered through a precursor solution to fabricate multiple copies of a photochemically-defined pattern, although a sequence of small steps might be required to effect large changes. Conversely, the individual traps in a holographic optical trap array can be moved independently by calculating and projecting a sequence of computer-generated diffraction patterns with each trap's position updated as required in each pattern. This would enable multiple traps to induce photochemical transformations in multiple regions simultaneously and would be useful for efficiently addressing multiple parts of one or more photochemically-defined structures. Benefits of the holographic optical trap technique in these applications include greatly improved throughput, and the opportunity to tailor initiation and growth propagation rates locally so as to optimize material properties in the finished product which might depend on such aspects of the formation process.

In the method of the invention the holographic optical traps are utilized by photopolymerizing Norland Type 73 UV-cured adhesive and Norland type 88 UV-cured adhesive- using light of wavelength 532 nm obtained from a frequency-doubled Nd:YVO$_4$ laser. Optical traps have also been used to photopolymerize polyacrylamide from a precursor solution containing a UV-excited photoinitiator and a free-radical inhibitor.

While preferred embodiments of the invention have been shown and described, it will be clear to those skilled in the art that various changes and modifications can be made without departing from the invention in its broader aspects as set forth in the claims provided hereinafter.

What is claimed is:

1. A method of incorporating particles of foreign matter into living cells having a cell wall or a cell membrane using an optical trapping system comprising:

providing a liposome having an outer leaf, and containing at least one particle of foreign matter within said liposome;

providing an optical trapping mechanism including a laser which emits a laser beam, said optical trapping system including a diffractive optical element which receives said laser beam and forms a plurality of separate laser beams, and providing a focusing element disposed downstream from said diffractive optical element;

wherein said diffractive optical element cooperates with said focusing element to separately converge each of the laser beams to form a focused spot or focal region to establish means for forming a separate first optical trap within the spot for each liposome containing said at least one particle of foreign matter using one of the separate laser beams for each at least one particle of foreign matter;

providing at least one living cell having a cell interior or cell membrane;

using a separate second optical trap produced by said optically trapping system, to hold and orient said cell in three dimensions;

using an optical scalpel to cut away enough of the cell wall or the cell membrane to expose a region of the cell wall or the cell membrane for subsequent liposome fusion;

using said first optical trap to move and orient the liposome in three dimensions, into proximity with the cell wall or cell membrane at the exposed region;

fusing the liposome to the cell by at least one of chemically fusing the liposome to the cell wall or cell membrane at the exposed region by action of proteins or other biochemical agents incorporated into the outer leaf of the liposome, or optically fusing the liposome to the cell membrane at the exposed region by using a pulse of laser light directed at an interface of the liposome-cell wall or cell membrane;

puncturing the liposome-cell wall or cell membrane interface after fusing of the liposome to the cell; and transferring the liposome's contents into the cell to move said at least one particle of foreign matter from said liposome into said cell interior while said liposome and said cell are held in said three dimensions by said respective first and said second optical traps.

2. The method as defined in claim 1 wherein the foreign matter is not endogenous to the cell.

3. The method as defined in claim 1 wherein the foreign matter comprises a hydrophilic substance.

4. The method as defined in claim 1 wherein the foreign matter comprises a nuclear acid molecule selected from the group consisting of RNA, DNA, PNA, a chimeric molecule and an expression vector.

5. The method as defined in claim 1 wherein the foreign matter is selected from the group consisting of a protein, polypeptide, a peptide, an amino acid, a hormone, a polysaccharide, a dye and a pharmaceutical agent.

6. The method as defined in claim 1 further including the step of recording microscope images during incorporation of foreign matter into the living cell.

7. The method as defined in claim 1 further including the step of controlling intensity of each of the laser beams to minimize multiphonon creation, thereby minimizing damage to the cell.

8. The method as defined in claim 1, wherein the at least separate first and second optical traps are holographic optical traps, and further comprising:

using digitally recorded microscope images to program a pattern of the separate at least first and second optical traps and their motions, to automate the incorporation method.

* * * * *